United States Patent
Lim et al.

(10) Patent No.: US 7,198,632 B2
(45) Date of Patent: Apr. 3, 2007

(54) OCCLUSION BALLOON CATHETER WITH LONGITUDINALLY EXPANDABLE BALLOON

(75) Inventors: Elaine Lim, Fremont, CA (US); Huey Quoc Chan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 178 days.

(21) Appl. No.: 10/792,076

(22) Filed: Mar. 2, 2004

(65) Prior Publication Data

US 2005/0197668 A1  Sep. 8, 2005

(51) Int. Cl.
*A61M 29/00* (2006.01)

(52) U.S. Cl. .................. 606/194; 604/916; 604/103.06

(58) Field of Classification Search ............. 604/96.01, 604/103.06–103.07, 103.09, 915, 916, 103.1, 604/103.11; 606/191–192, 194
See application file for complete search history.

(56) References Cited

U.S. PATENT DOCUMENTS

| | | | |
|---|---|---|---|
| 3,924,634 A * | 12/1975 | Taylor et al. .......... | 604/100.01 |
| 4,490,421 A | 12/1984 | Levy | |
| 4,573,966 A | 3/1986 | Weikl et al. | |
| 4,796,629 A | 1/1989 | Grayzel | |
| 4,798,586 A * | 1/1989 | Stevens .................... | 603/96.01 |
| 4,863,440 A | 9/1989 | Chin | |
| 4,906,244 A | 3/1990 | Pinchuk et al. | |
| 4,964,853 A * | 10/1990 | Sugiyama et al. ..... | 604/103.14 |
| 5,141,494 A | 8/1992 | Danforth et al. | |
| 5,545,209 A * | 8/1996 | Roberts et al. ............. | 623/1.11 |
| 5,695,468 A | 12/1997 | Lafontaine et al. | |
| 5,752,934 A | 5/1998 | Campbell et al. | |
| 5,797,948 A | 8/1998 | Dunham | |
| 5,868,705 A | 2/1999 | Bagaoisan et al. | |
| 6,039,721 A | 3/2000 | Johnson et al. | |
| 6,045,531 A | 4/2000 | Davis | |
| 6,110,142 A | 8/2000 | Pinchuk et al. | |
| 6,136,258 A | 10/2000 | Wang et al. | |
| 6,143,015 A | 11/2000 | Nobles | |
| 6,146,357 A | 11/2000 | Addis | |
| 6,248,121 B1 | 6/2001 | Nobles | |
| 6,293,924 B1 * | 9/2001 | Bagaoisan et al. ..... | 604/103.07 |
| 6,395,208 B1 | 5/2002 | Herweck et al. | |
| 6,425,908 B2 | 7/2002 | Ravenscroft et al. | |
| 6,458,096 B1 * | 10/2002 | Briscoe et al. ........... | 604/96.01 |
| 6,500,146 B1 | 12/2002 | Pinchuk et al. | |
| 6,500,148 B1 | 12/2002 | Pinchuk et al. | |

(Continued)

FOREIGN PATENT DOCUMENTS

EP  0 427 429 A2  5/1991

(Continued)

*Primary Examiner*—LoAn Thanh
(74) *Attorney, Agent, or Firm*—Crompton, Seager & Tufte, LLC

(57) ABSTRACT

Balloon catheters such as guide catheters can be configured to provide distal occlusion, while still providing sufficient interior lumen space for device delivery. Such catheters can provide a desired level of balloon expansion, yet prevent vessel damage caused by balloon over-expansion. A catheter can include an elongate shaft having a distal region, a proximal region and a lumen extending therebetween. A balloon is inflated to a desired expansion configuration with a desired diameter. Over-inflation of the balloon causes longitudinal expansion instead of increased radial expansion, thus maintaining the diameter of the balloon.

5 Claims, 4 Drawing Sheets

U.S. PATENT DOCUMENTS

| | | |
|---|---|---|
| 6,527,741 B1 | 3/2003 | Lee et al. |
| 6,554,795 B2 | 4/2003 | Bagaoisan et al. |
| 6,565,527 B1 | 5/2003 | Jonkman et al. |
| 6,599,266 B2 | 7/2003 | Morse |
| 6,626,861 B1 | 9/2003 | Hart et al. |
| 6,835,189 B2 * | 12/2004 | Musbach et al. ...... 603/103.07 |
| 2001/0008970 A1 | 7/2001 | Ravenscroft et al. |
| 2002/0128598 A1 | 9/2002 | Nobles |

FOREIGN PATENT DOCUMENTS

| | | |
|---|---|---|
| EP | 0 917 886 A1 | 5/1999 |

\* cited by examiner

OCCLUSION BALLOON CATHETER WITH LONGITUDINALLY EXPANDABLE BALLOON

TECHNICAL FIELD

The invention relates generally to catheters and more specifically to intravascular catheters that include an occlusion balloon to restrict blood flow during treatment.

BACKGROUND OF THE INVENTION

Balloon catheters are used in a number of surgical applications including occluding blood flow either distally or proximally of a treatment site. The inflation of the balloon must be controlled in order to avoid over expansion or rupture of the balloon, which may rupture or otherwise damage the vessel.

Reinforced balloons that only expand to a predetermined diameter are effective in reducing over-expansion of the balloon, but are limited to use in a specific sized vessel. Similarly, the use of a non-expandable sheath over the balloon may prevent over-inflation, but the size of the sheath limits the size of the vessel in which the system can be used.

A need remains for a balloon catheter that can provide the desired level of inflation while minimizing the risk of over-inflation.

SUMMARY OF THE INVENTION

The invention is directed to balloon catheters, such as those configured for providing proximal or distal occlusion, that minimize the risk of over-expansion while still providing sufficient inflation. In one embodiment, the balloon catheter has an elongate shaft with a lumen and an inflatable balloon disposed over a distal region of the shaft. The balloon includes a distal portion that is configured to expand to a first, desired, expansion configuration when a first amount of fluid is inserted into the balloon. When pressure in increased by adding more fluid such that the balloon is over-inflated, it expands to a second expansion configuration. The diameter of the inflated balloon in the first expansion configuration is substantially the same as the diameter of the over-inflated balloon in the second expansion configuration, yet force against the vessel wall does not increase substantially due to expansion of a proximal portion of the balloon which generally does not expand at the first pressure.

Accordingly, an example embodiment of the invention is a balloon catheter in which a proximal portion of the balloon is releasably attached to the shaft such that this proximal portion is released and inflated when excess inflation fluid is inserted into the balloon.

Another embodiment of the invention is a balloon catheter in which the proximal portion of the balloon is thicker than the distal portion such that injection of a first amount of inflation fluid causes the distal portion to inflate while the proximal portion remains in a collapsed configuration. When a greater amount of inflation fluid is injected into the balloon, the proximal portion inflates, resulting in increased longitudinal expansion while maintaining a substantially constant radial expansion against the vessel wall without excessive force that could cause damage or excessive pressure that could cause balloon failure.

The balloon catheter can be a multi-lumen catheter or a single lumen catheter. In a multi-lumen catheter, the balloon may be disposed such that it receives inflation fluid from an outer lumen, leaving an inner lumen available for delivery of various medical instruments or fluids. In a single lumen catheter, the balloon may be disposed such that a distal portion of the balloon overlies inflation ports in the catheter shaft, and a proximal portion of the balloon overlies a solid portion of the shaft.

BRIEF DESCRIPTION OF THE DRAWINGS

The invention may be more completely understood in consideration of the following detailed description of various embodiments of the invention in connection with the accompanying drawings, in which.

DETAILED DESCRIPTION

Figure 1:
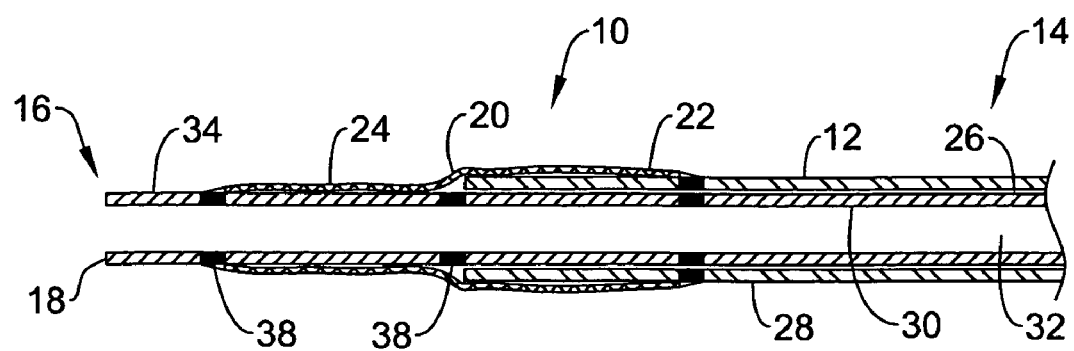
FIG. 1 is a cross-sectional view of the distal region of a balloon catheter in accordance with an embodiment of the invention.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a cross-sectional view of a catheter 10 in accordance with an embodiment of the invention. The catheter 10 can be one of a variety of different catheters, but is preferably an intravascular balloon catheter. Except as described herein, the catheter 10 can be manufactured using conventional techniques and materials. The intravascular catheter 10 can be sized in accordance with its intended use. The catheter 10 can have a length that is in the range of about 50 centimeters to about 150 centimeters and can have a diameter that is in the range of about 2 F (French) to about 11 F.

Figure 2:
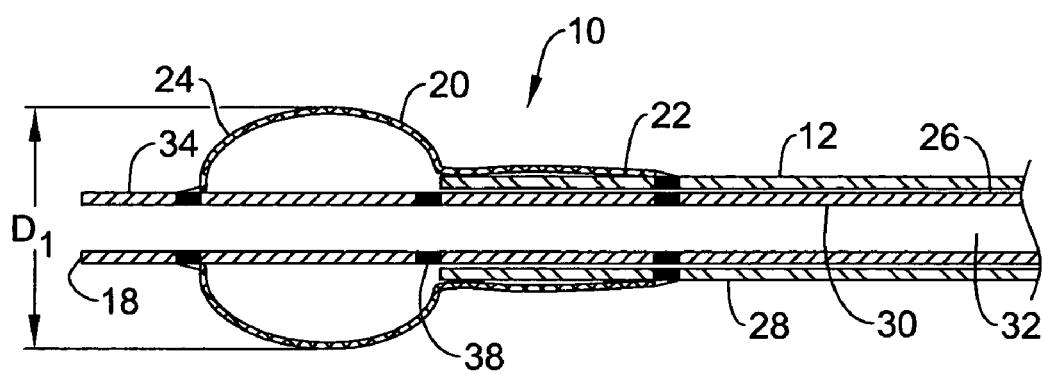
FIG. 2 is a cross-sectional view of the balloon catheter of FIG. 1 with the balloon inflated to a first inflation configuration.
Figure 3:
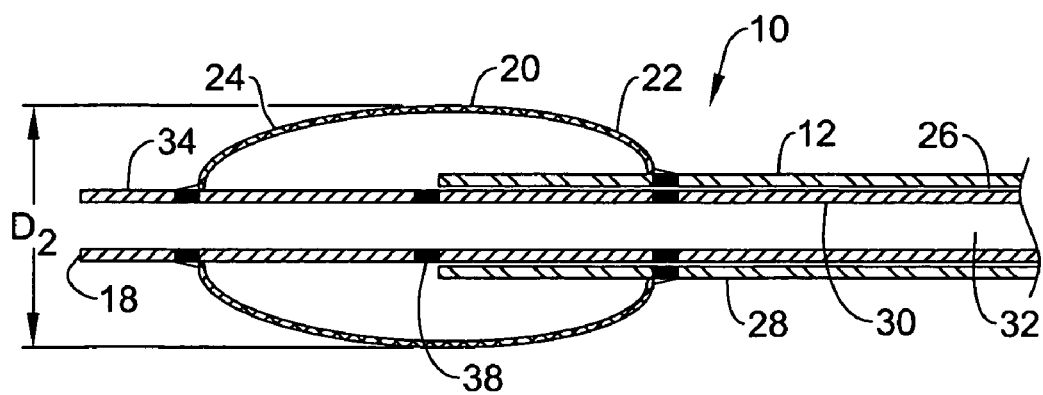
FIG. 3 is a cross-sectional view of the balloon catheter of FIG. 1 with the balloon inflated to a second inflation configuration.

In the embodiment illustrated in FIGS. 1–3, the intravascular catheter 10 is a coaxial multi-lumen catheter. Catheter 10 includes an elongate shaft 12 that has a proximal region 14, a distal region 16 and a distal end 18. The elongate shaft 12 includes an outer tubular member 28 and an inner tubular member 30. The inner tubular member 30 extends from the proximal region 14 of the elongate shaft 12 to the distal end 18 of the elongate shaft 12. The inner tubular member 30 defines a lumen 32 that extends through the elongate shaft 12. The outer tubular member 28 extends from the proximal region 14 to the location of the balloon 20. The balloon 20 has a proximal portion 22 and a distal portion 24. The proximal portion 22 is bonded to the outer tubular member 28 of the shaft 12 and the distal portion 24 of the balloon 20 is bonded to the inner tubular member 30. The outer tubular member 28 defines a second lumen 26 for inflating the balloon 20.

In some embodiments (not illustrated), the elongate shaft 12 can include one or more shaft segments having varying degrees of flexibility. For example, the elongate shaft 12 can include a proximal segment, an intermediate segment and a distal segment. In some embodiments, the elongate shaft 12 can also include a distal tip segment that can be formed from a softer, more flexible polymer. The elongate shaft 12 can include more than three segments, or the elongate shaft 12 can include fewer than three segments.

If the elongate shaft 12 has, for example, three segments, such as a proximal segment, an intermediate segment and a distal segment, each segment can include an inner tubular member 30 that is the same for each segment and an outer tubular member that becomes increasingly more flexible with proximity to the distal end 18 of the elongate shaft 12. For example, the proximal segment can have an outer tubular member that is formed from a polymer having a hardness of 72D (Durometer), the intermediate segment can have an outer tubular member that is formed from a polymer having a hardness of 63D and the distal segment can be formed from a polymer having a hardness of 40D.

If the elongate shaft 12 has three segments, each of the segments can be sized in accordance with the intended function of the resulting catheter 10. For example, the proximal segment can have a length of about 35 inches, the intermediate segment can have a length that is in the range of about 2 inches to about 3 inches, and the distal segment can have a length that is in the range of about 1 inch to about 1.25 inches.

The outer tubular member 28 can be a single layer having a lumen therethrough 26 that is sized to accommodate the outer surface 34 of the inner tubular member 30. In some embodiments, the outer tubular member 28 can have an outer diameter that is in the range of about 0.065 inches to about 0.13 inches and an inner diameter that is in the range of about 0.050 inches to about 0.12 inches. The outer tubular member 28 can have an overall length that is in the range of about 50 cm to about 150 cm.

The outer tubular member 28 can be formed of any suitable material such as a polymeric material. Polymers with low durometer or hardness can provide increased flexibility, while polymers with high durometer or hardness can provide increased stiffness. In some embodiments, the outer tubular member 28 can be formed of a material that will provide characteristics useful in providing column support to the elongate shaft 12 when the outer member is deployed thereon.

In some embodiments, the polymer material used is a thermoplastic polymer material. Some examples of some suitable materials include those discussed previously with respect to the outer tubular member 28 of the elongate shaft 12. By employing careful selection of materials and processing techniques, thermoplastic, solvent soluble, and thermosetting variants of these materials can be employed to achieve the desired results.

In some embodiments, the elongate shaft 12 can optionally include a reinforcing braid or ribbon layer to increase particular properties such as kink resistance. The distal part of the inner tubular member 30 can be made of polymers such as polytetrafluoroethylene (PTFE), better known as TEFLON®, or polyether block co-polyamide polymers such as PEBAX®. A reinforcement such as a platinum coil, stainless steel coil, or nitinol braid may also be used. An outer PEBAX® layer can be laminated over the reinforcement for kink resistance and to prevent the lumen 32 collapsing under negative pressure. Alternatively, a reinforcing braid or ribbon layer can be positioned between the outer tubular member 28 and the inner tubular member 30.

The inner surface of the outer tubular member 28 can be coated with a lubricious material to reduce friction between the inner surface of the outer tubular member 28 and the outer surface 34 of the inner layer 30. An exemplary material is TEFLON®.

In some embodiments (not illustrated), the outer tubular member 28 can be formed having two or more layers. In such embodiments, the outer tubular member 28 can have an inner layer that includes, is coated with, or formed from TEFLON®. The outer layer can be formed of any suitable polymer.

The inner tubular member 30 can be a uniform material and can define a lumen 32 that can run the entire length of the elongate shaft 12 and that is in fluid communication with a lumen (not illustrated) extending through a hub assembly. The lumen 32 defined by the inner tubular member 30 can provide passage to a variety of different medical devices, and thus, the inner tubular member 30 can include, be formed from or coated with a lubricious material, such as TEFLON®, to reduce friction within the lumen 32. The inner tubular member 30 can be dimensioned to define a lumen 32 having an appropriate inner diameter to accommodate its intended use. In some embodiments, the inner layer 30 can define a lumen 32 having a diameter of about 0.058 inches and the inner tubular member 30 can have a wall thickness of about 0.001 inches.

The outer tubular member 28 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer tubular member 28 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used. The outer layer 28 can have an inner diameter that is slightly larger than the outer diameter of the inner tubular member 30 to define second lumen 26.

In some embodiments, the outer tubular member 28 can have an inner diameter in the range of about 0.0600 inches to about 0.0618 inches and an outer diameter in the range of about 0.0675 inches to about 0.0690 inches. Part or all of the outer tubular member 28 can include materials added to increase the radiopacity of the outer layer 28, such as 50% bismuth subcarbonate.

The balloon 20 is positioned such that the distal portion 24 is attached to the outer surface 34 of inner tubular member 30 and the proximal portion 22 is attached to the outer tubular member 28 of the shaft 12. In the illustrated embodiment of FIG. 1, the balloon 20 is positioned such that approximately half of the balloon 20 is mounted over the outer layer 28 and approximately half of the balloon is mounted over the inner layer 30. The second lumen 26 provides means for introducing an inflation fluid into the balloon 20.

Figure 4:
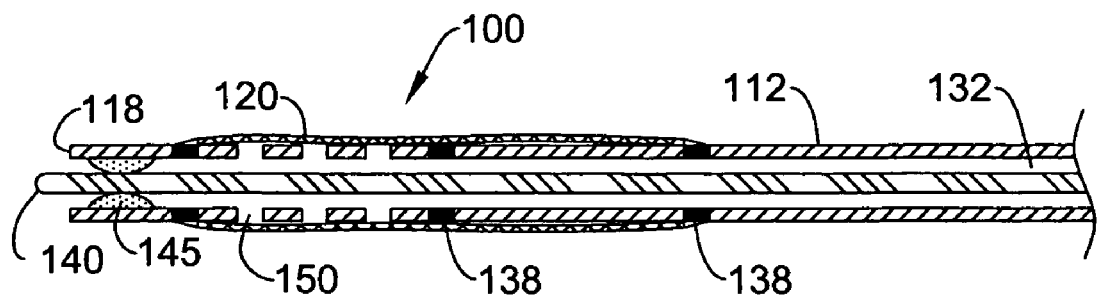
FIG. 4 is a cross-sectional view of the distal region of a balloon catheter in accordance with another embodiment of the invention.
Figure 5:
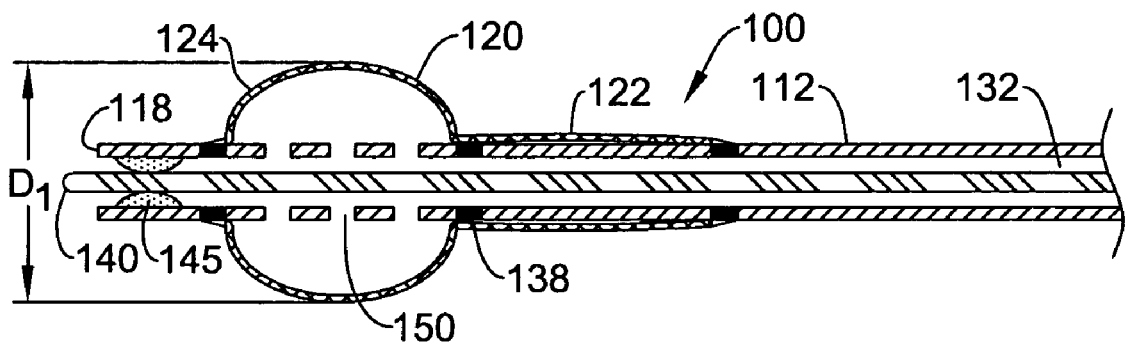
FIG. 5 is a cross-sectional view of the balloon catheter of FIG. 4 with the balloon inflated to a first inflation configuration.
Figure 6:
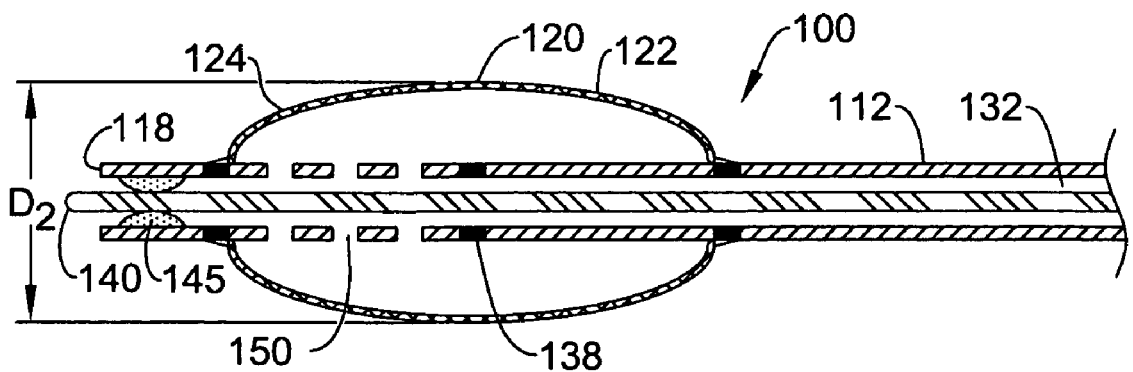
FIG. 6 is a cross-sectional view of the balloon catheter of FIG. 4 with the balloon inflated to a second inflation configuration.

FIGS. 4–6 illustrate a single lumen design of catheter 100 having an elongate shaft 112 including a common guidewire/inflation lumen 132 extending therethrough. The common lumen 132 accommodates the guidewire 140 and facilitates inflation and deflation of the balloon 120. A guidewire seal 145 is provided at the distal end 118 of the elongate shaft 112 to provide a fluid seal about the guidewire 140. With this arrangement, inflation fluid passes from the inflation syringe (not shown), through the common lumen 132 around the guidewire 140 disposed therein, through the inflation ports 150, and into the interior of the balloon 120 to facilitate inflation and deflation thereof. Markers 138 are disposed on the shaft 112 at the attachment points for the balloon 120, and at a position midway therebetween.

The balloon 120 is attached to the shaft 112 of the single lumen catheter 100 near the distal end 118 of the shaft 112. The distal portion 124 of the balloon 120 is attached to the shaft 112 distally of the inflation ports 150, and the proximal portion 122 of the balloon 120 is attached to the shaft 112 proximally of the inflation ports 150. The balloon 120 is positioned on the shaft 112 such that about one half of the balloon 120 overlies the portion of the shaft 112 with the inflation ports 150 and one half overlies the solid shaft 112.

The balloon 20 may be made of a highly compliant material that elastically expands upon pressurization. Because the balloon 20 elastically expands from the deflated state to the inflated state, the balloon 20 has an extremely low profile in the deflated state and does not require balloon folding as with other non-compliant or semi-compliant balloon materials. The balloon 20 may be formed of silicone, urethane polymer, or an extruded thermoplastic polyisoprene rubber such as a 40A durometer hydrogenated polyisoprene rubber, which is commercially available under the trade name Chronoprene™ from Carditech International, Inc.

Hydrogenated polyisoprene provides a balloon 20 having superior performance and manufacturing attributes. In particular, hydrogenated polyisoprene may be processed with standard polyolefin processing equipment to obtain balloon tubing having a wall thickness of approximately 0.001 inches to 0.010 inches and a corresponding inside diameter of approximately 0.016 inches to 0.028 inches. Such tubing has been demonstrated to produce balloons having a nominal outside diameter when inflated of approximately 3.0 mm to 5.5 mm.

The highly compliant balloon 20 preferably elastically expands at pressures less than 1.0 ATM. The highly compliant balloon 20 may have a pressure compliance of 2.0 mm/ATM or more at pressures less than 2.0 ATM. The highly compliant balloon 20 may have a volumetric compliance of approximately 0.3 mm per 0.01 ml to 0.5 mm per 0.01 ml at pressures less than 2.0 ATM, for balloons having a nominal diameter of approximately 3.5 mm and a length of approximately 10 mm to 15 mm.

The ends of the balloon 20 are attached to the shaft 12 using conventional bonding means such as thermal bonding using a laser. In one embodiment, the proximal portion 22 of the balloon 20 is releasably attached to the shaft 12 such that when a first amount of inflation fluid is introduced into the collapsed balloon, as shown in FIG. 1, the distal portion 24 of the balloon 20 inflates while the proximal portion 22 remains in an uninflated configuration. See FIG. 2. If an excess amount of inflation fluid is introduced into the balloon 20, the proximal portion 22 releases from the shaft 12 and inflates. See FIG. 3.

The releasable bond between the proximal portion 22 of the balloon 20 and the shaft 12 may be achieved by heating the balloon and/or the shaft 12 such that the proximal portion 22 of the balloon is adhered to the shaft 12 but is not permanently bonded. In an alternative embodiment, the proximal portion 22 of the balloon 20 can be releasably attached to the shaft 12 using an adhesive. The adhesive is selected to adhere the proximal portion 22 to the shaft 12 when the distal portion 24 is inflated to the desired diameter or pressure, but to release the proximal portion 22 when the distal portion 24 is over-inflated and the stress on the adhesive bond exceeds a predetermined threshold.

The degree of attachment is such that when the distal portion 24 of the balloon is inflated to the desired diameter, the proximal portion 22 remains adhered to the shaft 12, and is released only when the distal portion 24 is over-inflated.

Once the balloon is inflated to the desired pressure or diameter, inserting additional inflation fluid causes increased pressure and stress at the transition area between the inflated distal portion 24 and the releasably attached proximal portion 22. This increased stress causes the bond between the proximal portion 22 and the shaft 12 to be released, allowing the additional inflation fluid to inflate the proximal portion 22 of the balloon 20.

Figure 10:
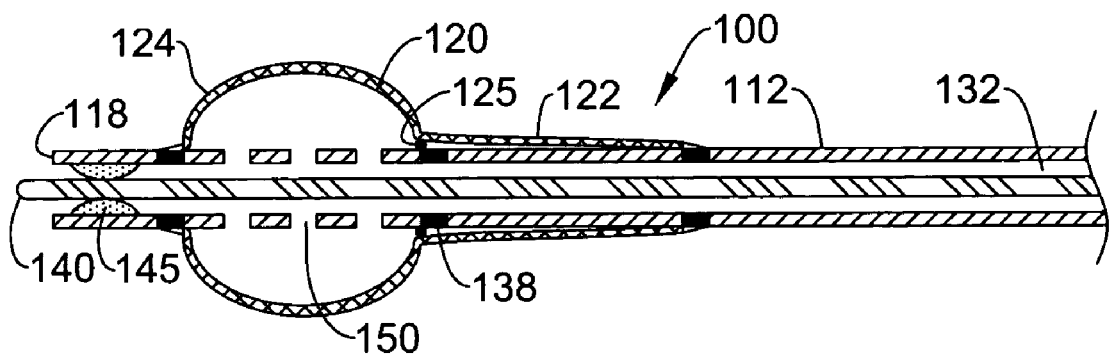
FIG. 10 is a cross-sectional view of a balloon catheter in accordance with another embodiment of the invention, inflated to a first configuration.

In one embodiment, the entire proximal portion 22 of the balloon 20 is releasably attached to the shaft 12. In another embodiment, the proximal portion 22 is releasably attached to the shaft 12 at least at the juncture between the distal portion 24 and proximal portion 22. In the embodiment illustrated in FIG. 10, the releasable attachment 125 is a discrete point of attachment at the juncture between distal and proximal portions of the balloon 120. Alternatively, the releasable attachment 125 can be an annular band at the juncture between distal and proximal portions of the balloon 120. In another embodiment, the releasable attachment 125 consists of multiple bands along the proximal portion 122. The releasable attachment 125 can also be multiple discrete points arranged about the shaft 112. In this embodiment, once the distal portion 124 of the balloon 120 is inflated, insertion of additional inflation fluid increases the pressure surrounding each discrete attachment point until the attachment points are broken and the proximal portion 124 of the balloon is inflated.

Figure 11:
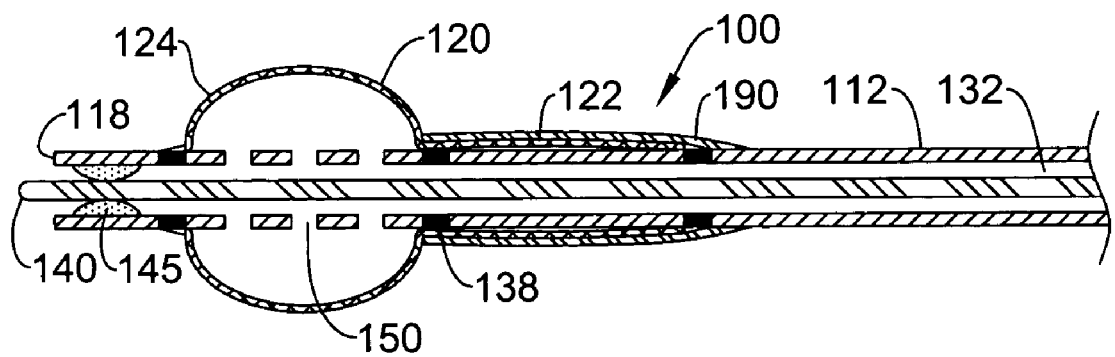
FIG. 11 is a cross-sectional view of a balloon catheter in accordance with another embodiment of the invention, inflated to a first configuration.

In another embodiment, illustrated in FIG. 11, a sheath 190 is disposed over the proximal portion 122 of the balloon 120. The sheath 190 can be attached to the shaft 112 proximally of the proximal portion 122 of the balloon 120. In one embodiment, the sheath 190 is not attached to the shaft 112. The sheath 190 can be made of an elastomeric material similar to or different from the material from which the balloon 120 is made. In one embodiment, the sheath 190 can be bonded, laminated or otherwise attached to the proximal portion 122 of the balloon 120. The sheath 190 impedes the inflation of the proximal portion 122 of the balloon 120 such that an increased amount of inflation fluid or increased pressure is necessary for the proximal portion 122 of the balloon 120 to inflate under the sheath 190.

In an alternative embodiment, the sheath 190 can be made of a material that can be broken, torn, or ruptured under pressure. The strength of the sheath 190 is such that it remains intact, keeping the proximal portion 122 of the balloon 120 in a deflated configuration until the pressure at the juncture between the distal and proximal portions of the balloon exceeds a predetermined threshold. The sheath 190 then breaks, tears or ruptures, allowing the proximal portion 122 of the balloon 120 to inflate.

The additional longitudinal balloon area provided by the released proximal portion 22 of the balloon 20 allows for a substantial amount of excess inflation fluid to be held by the balloon 20 without increasing the balloon diameter. This is shown in FIGS. 2 and 3, where the diameter $D_1$ of the balloon 20 with just the distal portion 24 inflated is substantially the same as the diameter $D_2$ of the balloon 20 with both the distal portion 24 and the proximal portion 22 inflated.

The amount of over-inflation protection achieved by the balloon can be adjusted by varying the amount of the proximal portion 22 of the balloon 20 that is releasably attached to the shaft 12. In the embodiment illustrated in the figures, the proximal portion 22 that is releasably attached to the shaft 12 is approximately one half the length of the balloon 20. A greater amount of protection is provided by releasably attaching a larger percentage of the balloon to the shaft. The length of the balloon and the length of the proximal portion that is releasably attached to the shaft is selected to achieve the desired diameter of the initially inflated distal portion 24 and the amount of over-inflation protection needed for a particular surgical procedure.

Figure 7:
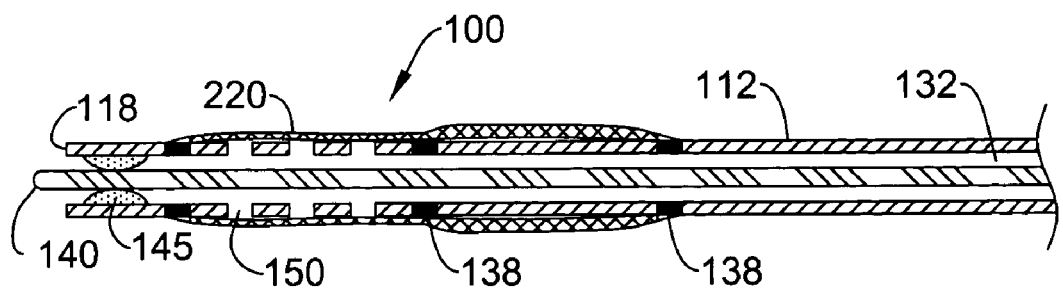
FIG. 7 is a cross-sectional view of the distal region of a balloon catheter in accordance with another embodiment of the invention.
Figure 8:
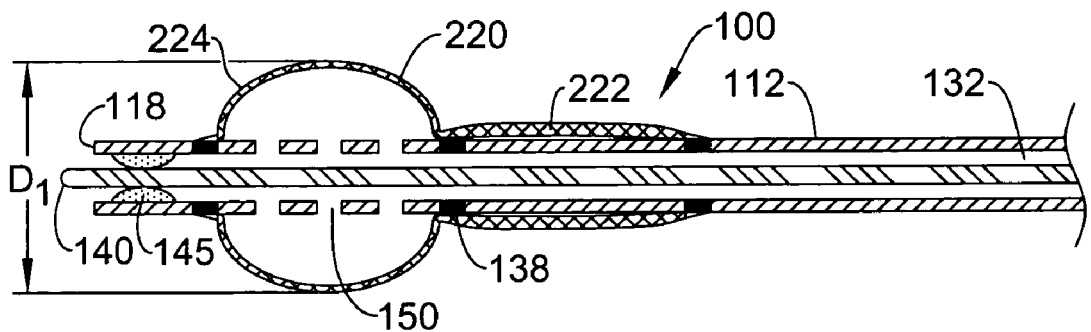
FIG. 8 is a cross-sectional view of the balloon catheter of FIG. 7 with the balloon inflated to a first inflation configuration.
Figure 9:
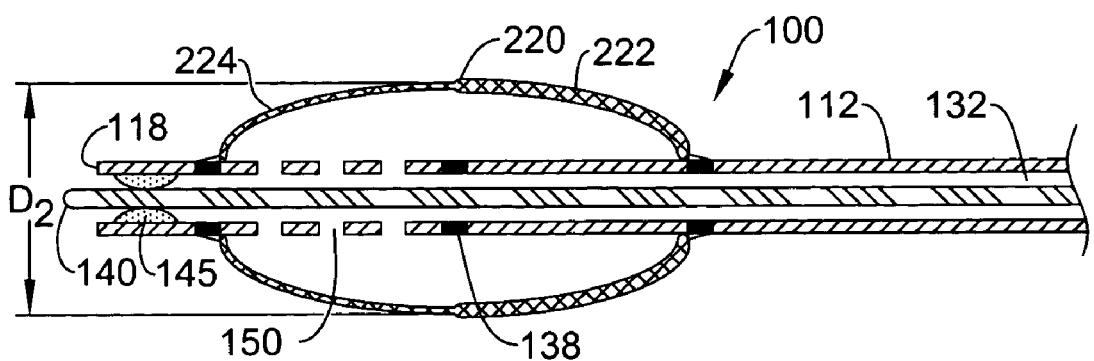
FIG. 9 is a cross-sectional view of the balloon catheter of FIG. 7 with the balloon inflated to a second inflation configuration.

In another embodiment as illustrated in FIGS. 7–9, the proximal portion 222 of the balloon 220 has a wall thickness that is greater than a wall thickness of the distal portion 224 of the balloon 220. The increased thickness in the proximal portion 222 requires a greater pressure to achieve inflation. The distal portion 224 is inflated by injecting a first amount of inflation fluid into the balloon 220. The amount of pressure necessary to achieve inflation of the distal portion 224 is insufficient to inflate the proximal portion 222. Once the distal portion 224 of the balloon 220 is inflated to the desired pressure or diameter, injection of additional inflation fluid causes the pressure in the balloon 220 to increase, resulting in inflation of the proximal portion 222.

The difference in thickness between the distal portion 224 and proximal portion 222 of the balloon 220 is selected to achieve the desired inflation characteristics. In one embodiment, the distal portion 224 is about half the thickness of the proximal portion 222. In another embodiment, the distal portion 224 is about one-third the thickness of the proximal portion 222.

The balloon 220 can be made using conventional techniques including molding, extruding, stretching, etc., to achieve the desired difference in thickness between the distal 224 and proximal 222 portions. In one embodiment, the distal 224 and proximal 222 portions are about equal in length. In alternative embodiments, the proximal portion 222 is longer than the distal portion 224 to provide a greater safety measure against over-inflation. The proximal portion 222 can also be shorter than the distal portion 224.

Radiopaque marker bands 38 may be disposed on the elongate shaft 12 adjacent to the connection between the balloon 20 and the elongate shaft 12 to facilitate radiographic positioning of the balloon 20. An additional marker band 38 may be disposed midway between the distal and proximal marker bands 38. The marker bands 38 may be solid or split bands of platinum or other radiopaque metal. Radiopaque materials are understood to be materials capable of producing a relatively bright image on a fluoroscopy screen or another imaging technique during a medical procedure. This relatively bright image aids the user of device in determining its location. Some examples of radiopaque materials can include, but are not limited to, gold, platinum, iridium, palladium, tantalum, tungsten alloy, plastic material loaded with a radiopaque filler, and the like.

In use, the catheter 10, 100 is inserted to the desired location with the balloon 20, 120 in a collapsed configuration, as seen in FIGS. 1 and 4. An inflation fluid is injected through the second lumen 26 of a multi-lumen catheter 10 or the single lumen 132 in a single lumen catheter 110. Inflation fluid is injected until the distal portion 24, 124 of balloon 20, 120 is expanded to the desired diameter $D_1$ in the first expansion configuration, seen in FIGS. 2 and 5. The distal and center markers 38, 138 are used as a guide for determining when the distal portion 24, 124 of the balloon 20, 120 is at the desired inflation configuration.

If excess inflation fluid is inserted, the proximal portion 22, 120 of the balloon 20, 120 is released, and the balloon 20, 120 is inflated to the second expansion configuration, as shown in FIGS. 3 and 6. By comparing FIGS. 2 and 5 with FIGS. 3 and 6, respectively, it is clear that the first diameter $D_1$ of the balloon 20, 120 in the desired first inflation configuration is substantially the same as the diameter $D_2$ of the balloon 20, 120 in the second, over-inflation configuration. This longitudinal expansion provides a safety measure in that it prevents the over-inflated balloon 20, 120 from achieving an excessive diameter, resulting in damage or rupture of the vessel.

The balloon 20 can be sized as appropriate to fit over the elongate shaft 12, as well as to nearly or completely occlude a particular vasculature in which the balloon 20 will be used. In some embodiments, the balloon 20 can have a length that is in the range of about 0.5 cm to about 2 cm. The balloon 20 can have a first diameter (desired first expansion configuration) that is in the range of about 1 mm to about 1.5 cm. The balloon can have an average thickness that is in the range of about 0.001 inches to about 0.002 inches.

In some embodiments, part or all of catheter 10 can include a lubricious coating. Lubricious coatings can improve steerability and improve lesion-crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding and solubility. In some embodiments, a distal portion of the catheter can be coated with a hydrophilic polymer, while the more proximal portions can be coated with a fluoropolymer.

It should be understood that this disclosure is, in many respects, only illustrative. Changes may be made in details, particularly in matters of shape, size and arrangement of steps, without exceeding the scope of the invention. The invention's scope is, of course, defined in the language in which the appended claims are expressed.

The invention claimed is:

1. A balloon catheter comprising:
an elongate shaft having a distal region and a proximal region and defining a lumen therebetween; and
an inflatable balloon disposed over a portion of the distal region of the elongate shaft, the balloon having distal and proximal portions and distal and proximal ends;
wherein the balloon is configured to expand to a first expansion configuration when a first amount of fluid is inserted into the balloon, and to expand to a second expansion configuration when a second, greater, amount of fluid is inserted into the balloon; wherein when the balloon is in the first expansion configuration, the distal portion of the balloon is expanded and the proximal portion of the balloon is in a collapsed configuration;
wherein the proximal portion of the balloon is releasably attached to the shaft;
wherein the proximal portion of the balloon is heat bonded to the shaft for releasably attaching to the shaft.

2. A catheter assembly comprising:
an elongate shaft having a distal region and a proximal region and a lumen disposed therebetween;
an expandable balloon disposed about the distal region of the shaft;
wherein the balloon is configured such that as an inflation fluid is inserted into the balloon, the balloon is expanded from a completely collapsed configuration to a partially inflated configuration and then to a fully inflated configuration; wherein a diameter of the balloon in the partially inflated configuration is substantially the same as a diameter of the balloon in the fully inflated configuration;
wherein in the partially inflated configuration a first portion of the balloon is inflated while a second portion of the balloon remains uninflated,and in the fully inflated configuration, both the first and second portions of the balloon are inflated;
wherein the balloon has first and second ends bonded to the shaft; wherein the second portion of the balloon is releasably attached to the shaft;
wherein the second portion of the balloon is heat bonded to the shaft for releasably attaching to the shaft.

3. A catheter assembly comprising:
an elongate shaft having a distal region and a proximal region and a lumen disposed therebetween;
an expandable balloon disposed about the distal region of the shaft;
wherein the balloon is configured such that as an inflation fluid is inserted into the balloon, the balloon is expanded from a completely collapsed configuration to a partially inflated configuration and then to a fully inflated configuration; wherein a diameter of the balloon in the partially inflated configuration is substantially the same as a diameter of the balloon in the fully inflated configuration;
wherein in the partially inflated configuration a first portion of the balloon is inflated while a second portion of the balloon remains uninflated, and in the fully inflated configuration, both the first and second portions of the balloon are inflated;
wherein the balloon has first and second ends bonded to the shaft; wherein the second portion of the balloon is releasably attached to the shaft;
wherein the second portion of the balloon is releasably attached to the shaft with a releasable adhesive.

4. A balloon catheter comprising:
an elongate shaft having a distal region and a proximal region and defining a lumen therebetween; and
an inflatable balloon disposed over a portion of the distal region of the elongate shaft, the balloon having a first longitudinal portion and a second longitudinal portion and distal and proximal ends;
wherein the balloon is configured for the first longitudinal portion to expand to a first expansion configuration when a first amount of fluid is inserted into the balloon, and for the second longitudinal portion to expand when a second, greater, amount of fluid is inserted into the balloon;
wherein the second longitudinal portion of the balloon is releasably attached to the shaft;
wherein the second longitudinal portion of the balloon is heat bonded to the shaft for releasably attaching to the shaft.

5. A balloon catheter comprising:
an elongate shaft having a distal region and a proximal region and a lumen therebetween; and
an inflatable balloon disposed over a portion of the distal region of the elongate shaft, the balloon having a first longitudinal portion and a second longitudinal portion and distal and proximal ends;
wherein the balloon is configured for the first longitudinal portion to expand to a first expansion configuration when a first amount of fluid is inserted into the balloon, and for the second longitudinal portion to expand when a second, greater, amount of fluid is inserted into the balloon;
wherein the second longitudinal portion of the balloon is releasably attached to the shaft;
wherein the second longitudinal portion of the balloon is releasably attached to the shaft with a releasable adhesive.

* * * * *

UNITED STATES PATENT AND TRADEMARK OFFICE
CERTIFICATE OF CORRECTION

| | | |
|---|---|---|
| PATENT NO. | : 7,198,632 B2 | Page 1 of 1 |
| APPLICATION NO. | : 10/792076 | |
| DATED | : April 3, 2007 | |
| INVENTOR(S) | : Elaine Lim et al. | |

It is certified that error appears in the above-identified patent and that said Letters Patent is hereby corrected as shown below:

Column 10
Line 44, after "region and" and before "a lumen", insert -- defining --.

Signed and Sealed this

Nineteenth Day of June, 2007

JON W. DUDAS
*Director of the United States Patent and Trademark Office*